United States Patent
Hisanaka

(10) Patent No.: US 7,858,840 B2
(45) Date of Patent: Dec. 28, 2010

(54) ABSORBENT ARTICLE CONTAINING SKIN-PROTECTIVE INGREDIENT

(75) Inventor: Takayuki Hisanaka, Kagawa (JP)

(73) Assignee: Uni-Charm Corporation, Kawanoe-shi (JP)

(*) Notice: Subject to any disclaimer, the term of this patent is extended or adjusted under 35 U.S.C. 154(b) by 125 days.

(21) Appl. No.: 09/761,511

(22) Filed: Jan. 16, 2001

(65) Prior Publication Data
US 2001/0009991 A1    Jul. 26, 2001

(30) Foreign Application Priority Data
Jan. 25, 2000    (JP) ............................. 2000-015404

(51) Int. Cl.
*A61F 13/15* (2006.01)

(52) U.S. Cl. .................. 604/364; 604/367; 604/385.28

(58) Field of Classification Search ................ 604/364, 604/367, 381, 385.24, 385.28
See application file for complete search history.

(56) References Cited

U.S. PATENT DOCUMENTS

| | | | | |
|---|---|---|---|---|
| 3,859,125 A * | 1/1975 | Miller et al. | ............. | 229/164.2 |
| 4,740,402 A * | 4/1988 | Maeda et al. | ............... | 428/35.9 |
| 4,753,643 A | 6/1988 | Kassai | .......................... | 604/359 |
| 4,790,836 A | 12/1988 | Brecher | ....................... | 604/359 |
| 4,959,059 A | 9/1990 | Eilender et al. | ............. | 604/358 |
| 5,268,222 A * | 12/1993 | Honeycutt | .................. | 112/440 |
| 5,607,760 A * | 3/1997 | Roe | ........................ | 428/319.7 |
| 6,120,488 A * | 9/2000 | VanRijswijck et al. | ...... | 604/364 |
| 6,120,783 A * | 9/2000 | Roe et al. | .................... | 424/402 |
| 6,156,024 A * | 12/2000 | Schulte et al. | ............... | 604/304 |
| 6,160,200 A | 12/2000 | Ehrnsperger et al. | ........ | 604/378 |
| 6,166,285 A * | 12/2000 | Schulte et al. | .............. | 604/364 |
| 6,290,979 B1 * | 9/2001 | Roe et al. | .................... | 424/402 |

FOREIGN PATENT DOCUMENTS

| | | |
|---|---|---|
| JP | H-10-509895 | 9/1998 |
| JP | H-10-509896 | 9/1998 |
| WO | 98/24390 | 6/1998 |
| WO | WO 98/24390 | 6/1998 |
| WO | 98/42286 | 10/1998 |
| WO | WO 98/42286 | 10/1998 |
| WO | 99/25287 | 5/1999 |
| WO | WO 99/25287 | 5/1999 |

OTHER PUBLICATIONS

Elert, Glenn; Temperature of a Healthy Human (Skin Temperature); 2001.*
European Search Report and Annex.

* cited by examiner

*Primary Examiner*—Patricia M Bianco
*Assistant Examiner*—Lynne Anderson
(74) *Attorney, Agent, or Firm*—Morrison & Foerster LLP

(57) ABSTRACT

Provided is an absorbent article including a main body having a liquid-pervious top sheet, a back sheet and an absorbent core sandwiched between the top sheet an the back sheet; a layer containing a skin-protective ingredient; and a support layer for covering the ingredient-containing layer. The ingredient-containing layer and the support layer are provided on the surface of the main body to be in contact with the skin of a wearer. The solubility in water of the support layer is promoted at 25° C. or higher, and/or the moisture absorbability or the solubility in water of the support layer is promoted at a relative humidity of at least 30%.

8 Claims, 3 Drawing Sheets

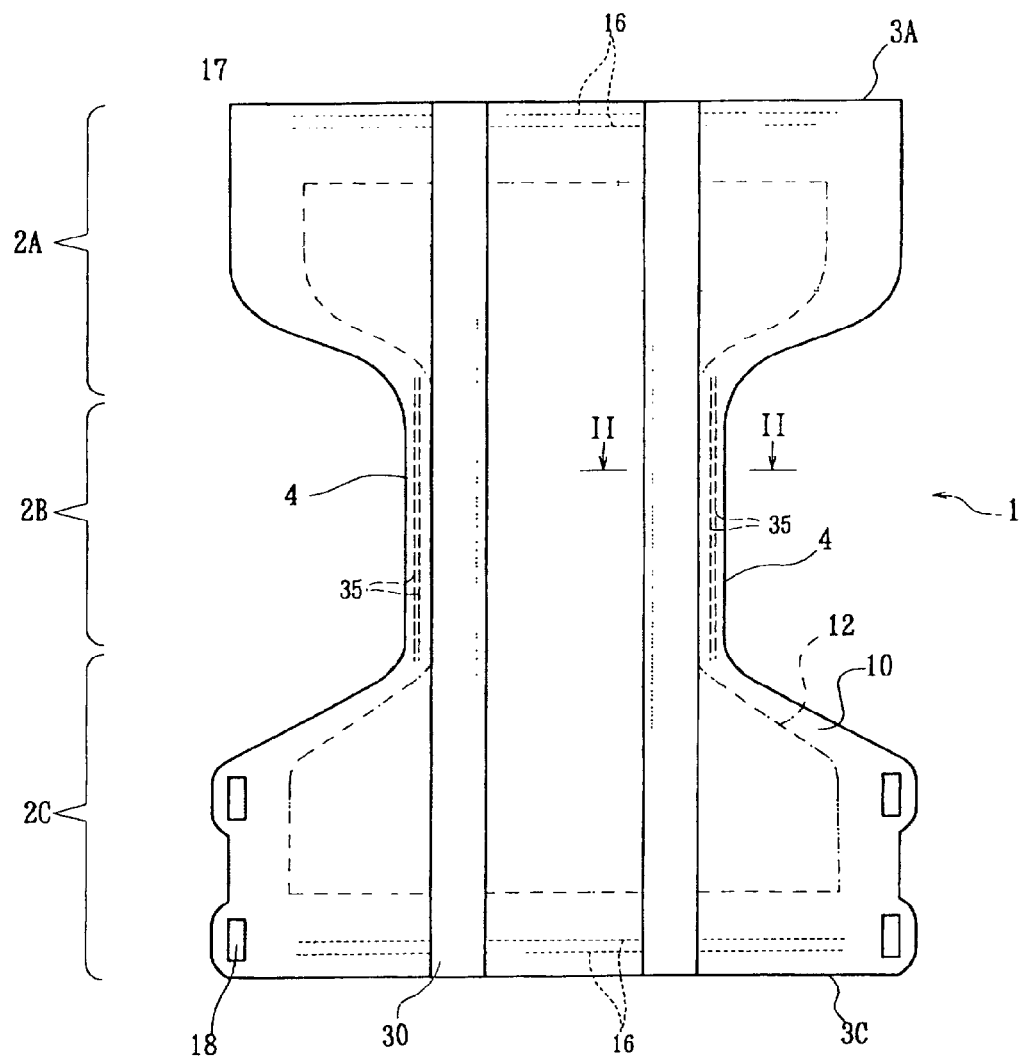
Fig. 1
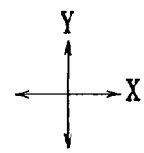

ABSORBENT ARTICLE CONTAINING SKIN-PROTECTIVE INGREDIENT

BACKGROUND OF THE INVENTION

1. Field of the Invention

The present invention relates to an absorbent article for disposable diapers, sanitary napkins, pantiliners, incontinence pads, etc. More precisely, it relates to such an absorbent article capable of transferring a skin-protective ingredient to the skin of users.

2. Description of the Related Art

Recently, various absorbent articles of absorbing excretions are used, including, for example, disposable diapers, sanitary napkins, pantiliners, incontinence pads, etc. While worn, such absorbent articles are wetted by wearer's excretions such as sweat, urine, feces, menses and other vaginal discharges, etc., and will often give a stuffy feel to wearers and irritate the skin of wearers (i.e., diaper rash and the like). In particular, in the private parts and therearound that are to be in direct contact with excretions, and also in the area to be in direct contact with an elastic member of an absorbent article, for example, in the waist and therearound and also in the thighs and therearound for the diapers, the problem is serious. Lotion or cream that contains a skin-protective ingredient is often applied to the skin of a wearer in order to prevent the wearer's skin from being stuffed and irritated by such a wetted absorbent article. However, this is still problematic in that such lotion or cream soils the hand and using it is troublesome. In particular, babies and aged persons who could not apply it to their own skin by themselves need caregivers' aid, which, however, is troublesome.

To solve the problems set forth above, International Unexamined Patent Publication (Kohyo) Nos. Heisei 10-509895 and 10-509896 disclose a diaper of which top sheet is coated with a lotion composition. The lotion composition comprises a mixture of a skin-protective emollient and a passivator capable of being fluidized at a predetermined temperature. In this, however, the passivator will be fluidized at such a predetermined temperature even during storage or transportation of the diaper, and, as a result, the necessary emollient will flow away before use. If so, the amount of the emollient to be effective while the diaper is actually worn will be reduced. Another problem with the diaper is that the lotion composition used for it is insoluble in water. When the fluidized lotion composition has spread over the top sheet of the diaper, it will lower the liquid permeability of the top sheet, and, as a result, the absorptive power of the diaper will be thereby lowered.

SUMMARY OF THE INVENTION

An object of the present invention is to provide an absorbent article capable of effectively transferring a skin-protective ingredient to the skin of a wearer.

Another object of the invention is to provide an absorbent article capable of transferring a skin-protective ingredient to the skin of a wearer without lowering the absorptive power of the absorbent article.

According to an aspect of the invention, an absorbent article may comprise: a main body including a liquid-pervious top sheet, a back sheet and an absorbent core sandwiched between the top sheet an the back sheet; a layer containing a skin-protective ingredient; and a support layer for covering the ingredient-containing layer, the ingredient-containing layer and the support layer being provided on the surface of the main body to be in contact with the skin of a wearer, wherein;

the solubility in water of the support layer is promoted at 25° C. or higher, and/or the moisture absorbability or the solubility in water of the support layer is promoted at a relative humidity of at least 30%.

The absorbent article of the invention includes the main body in which a layer (lower layer) containing a skin-protective ingredient and a support layer (upper layer) for covering the ingredient-containing layer are located on the surface thereof to be in contact with the skin of a wearer. The support layer (upper layer) supports the skin-protective ingredient contained in the lower layer until the ingredient is needed. For example, when the absorbent article is wetted by the sweat or excretions of a wearer to have high humidity therein, the support layer is fluidized or is dissolved in water, whereby the lower layer or the skin-protective ingredient contained in the lower layer is exposed outside, and the skin-protective ingredient adheres to the skin of the wearer. Accordingly, in the absorbent article of the invention, the skin-protective ingredient adheres to the skin of a wearer at proper time or only when it is needed, and the ingredient does not adhere to any other part except for the skin and is wasted little. In addition, in the invention, when the support layer is soluble in water, it retards little the liquid permeability of the top sheet even if the two layers are provided on the surface of the main body of the absorbent article.

The support layer may be formed of at least one compound selected from the group consisting of polyethylene oxide having a molecular weight of from 100 to 500,000, polypropylene glycol having a molecular weight of from 100 to 10,000, and polyvinyl alcohol having a degree of polymerization of from 300 to 4000 and a degree of saponification of from 50 to 99.

Preferably, the layer containing the skin-protective ingredient is formed of a compound capable of forming an oily film on the skin of a wearer. Also preferably, the layer containing the skin-protective ingredient can be fluidized at 35° C. or higher.

The layer containing the skin-protective ingredient may be formed of at least one compound selected from the group consisting of liquid polyisoprene, squalane, pristane, ozocerite, ceresine, microcrystalline wax, polyethylene powder, liquid paraffin, vaseline, and paraffin.

The two layers may be located on the surface of the top sheet. If desired, the absorbent article may further include a leak-preventive cuff for preventing side leakage and/or a leg cuff for preventing leakage through the area around the wearer's thighs, and the two layers are located on the surface of the leak-preventive cuff and/or the leg cuff.

BRIEF DESCRIPTION OF THE DRAWINGS

FIG. 1 is a plan view of a diaper, as one embodiment of an absorbent article according to the invention, looking from a liquid-receiving side;

DESCRIPTION OF THE PREFERRED EMBODIMENTS

Figure 2:
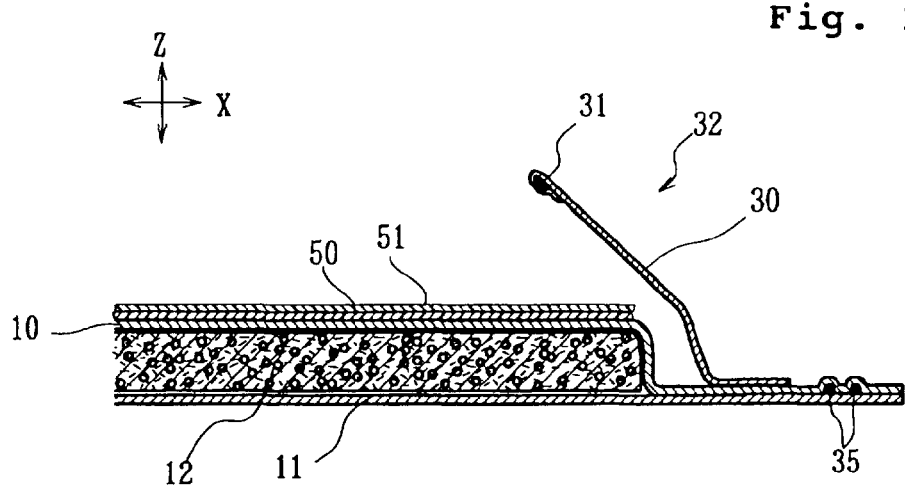
FIG. 2 is a cross-sectional view of the diaper of FIG. 1, cut along the line II-II.

A disposable diaper, one embodiment of the absorbent article of the invention is described with reference to the accompanying drawings. FIG. 1 is a plan view of the diaper, with its liquid-receiving side being in front; and FIG. 2 is a cross-sectional view of the diaper of FIG. 1, cut along the line II-II.

As shown in FIG. 1, a disposable diaper 1 of the invention is a hour-glass shaped, open diaper. The disposable diaper is composed of a front area 2A to be fitted to the abdominal region of a wearer, a back area 2C to be fitted to the buttocks and/or the back thereof, and a center area 2B to be fitted to the crotch thereof. In this, the direction extending from the front area to the back area via the crotch area is designated by Y (this is a longitudinal direction of the diaper); and the direction perpendicular to the direction Y is designated by X (this is a transverse direction of the diaper). As shown in FIG. 2, the direction extending toward the wearer is designated by Z.

The disposable diaper 1 comprises a main body including a liquid-pervious top sheet 10 to be faced the skin of the wearer, a liquid-impervious back sheet 11 to be faced an external support such as an underwear, and an absorbent core 12 sandwiched between the top sheet 10 and the back sheet 11. The main body including the top sheet 10, the back sheet 11 and the absorbent core 12 is in the form of a hour-glass. Around the absorbent core 12 between them, the top sheet 10 and the back sheet 11 are bonded to each other with a hot-melt adhesive.

When the diaper 1 is worn, back flaps from the back area 2C (the back flaps are portions that protrude in the direction X) are respectively laid on the back sheet 11 in the front area 2A, and fastener sheets 18 provided on both edge portions of the top sheet 10 in the back flaps from the back area 2C are fastened with fastener portions 17 provided on the back sheet 11 in front flaps (the front flaps are portions that protrude in the direction X) from the front area 2A, around the waist of a wearer. While the diaper 1 is thus worn, an elastic member 16 provided around the waist elastically expands and contracts, and, as a result, the diaper 1 is well fitted to the body of the wearer.

The diaper 1 of the invention is provided with a liquid-impervious strip sheet 30 on the side edge portions 4, 4 of the top sheet 10; and one side edge of the strip sheet 30 adjacent to the center of the diaper 1 is provided with an elastic member 31. The other side edge of the strip sheet 30 and the remaining two opposite end edges thereof are all bonded to an outer surface of the top sheet 10 to form a pair of leak-preventive cuffs 32. While the diaper 1 is worn, the side edge of each cuff 32 adjacent to the center of the diaper 1 rises up to prevent side leakage, and the upper side in the direction Z of the leak-preventive cuff 32 is kept in contact with the skin of the wearer.

In the region-of the side edge portions 4, 4 in the direction X of the diaper 1 in which the absorbent core 12 does not exist (this is outside the absorbent region of the diaper 1), an elastic member 35 extending in the direction Y of the diaper 1 is bonded and fixed to the diaper 1 between the top sheet 10 and the back sheet 11. The elastic member 35 elastically expands and contracts in the direction Y, whereby the top sheet 10 and the back sheet 11 are elastically expanded and contracted at the side edge portions 4, 4 in the direction X of the diaper 1. While the diaper 1 is worn, the elastic member 35 thus forms a pair of leg cuffs that are kept in contact with the thighs of the wearer.

In the region of the diaper 1 of the invention where the absorbent core 12 exists, a layer 50 that contains a skin-protective ingredient is provided on the surface of the top sheet 10 that receives the excretions discharged by a wearer, and a support layer 51 is stacked thereon to cover the surface of the layer 50.

Preferably, the layer 50 is formed of a compound capable of forming an oily film on the uppermost surface of the skin of a wearer so as to protect the wearer's skin from being irritated. The oily film thus formed on the wearer's skin can protect the skin from being irritated by the chemical stimulation caused by excretions and surfactant and by the physical stimulation caused by the contact of the diaper to the skin. The compound to form such an oily film may be liquid, semi-solid (waxy) or solid at 25° C. For its properties, however, the compound is preferably liquid or semi-solid at 25° C. or higher, more preferably at 35° C. or higher, in order that it may well spread on the skin to form an oily film thereon. Contrary to this, compounds that could not be still liquid or semi-solid even at temperatures higher than ordinary human body temperature, for example, at 40° C. or higher are unfavorable, since they could hardly form the intended oily film. Accordingly, it is desirable that the oily film-forming compound for use in the invention is liquid or semi-solid at 40° C. or lower, more preferably at 37° C. or lower.

Also preferably, the oily film-forming compound is insoluble in water, in order that the oily film formed by it on the skin does not dissolve in the wearer's sweat and excretions and does not flow away. However, the compound may be emulsified in water, when mixed and shaken with water. Still preferably, the compound has a hydrophilic group. This is because, even if the compound having a hydrophilic group has widely spread over the surface of the top sheet 10, it will hardly lower the liquid permeability of the top sheet 10. Since the oily film-forming compound is kept in direct contact with the skin of a wearer, it is desirable that the compound is colorless or white, or is nearly colorless or whitish.

Concrete examples of the oily film-forming compound are mentioned below, which, however, are not limitative. Needless to say, any other compounds not mentioned below are employable herein, so far as they have the ability to form an oily film. One or more of the compounds mentioned below may be used herein either singly or as combined.

(1) Vegetable Based Oils:

Drying oils such as grape seed oil, safflower oil, soybean oil, etc.; semi-drying oils such as sesame oil, corn oil, cotton seed oil, rape seed oil, sunflower oil, etc.; non-drying oils such as avocado oil, almond oil, olive oil, sasanqua oil, camellia oil, persic oil, peanut oil, etc. Of these, preferred are semi-drying oils and non-drying oils in view of their time-dependent stability.

(2) Vegetable Based Fats:

Cacao butter, palm oil, palm kernel oil, haze tallow, coconut oil, etc.

(3) Animal Based Oils and Fats:

Turtle oil, mink oil, egg yolk oil, beef tallow, lard, etc.

(4) Fish Based Oils:

Sardine oil, saury oil, mackerel oil, menhaden oil, etc.

(5) Animal Based Waxes:

Whale wax, bees wax, lanolin, etc.

(6) Vegetable Based Waxes:

Carnauba wax, candelilla wax, jojoba oil, etc.

(7) Hydrocarbons:

Liquid polyisoprene, squalane, pristane, ozocerite, ceresine, microcrystalline wax, polyethylene powder, liquid paraffin, VASELINE™ (i.e., petroleum jelly), paraffin, etc.

(8) Derivatives from the Oily Components (1) to (7) Prepared by Hydrogenating the Unsaturated Part of the Components.

Among the oily film-forming compounds set forth above, preferred are oils and fats generally used in cosmetics as they do not irritate the skin. More preferred is vaseline, as inexpensive and safe.

The layer 50 comprising an oily film-forming compound as set forth above may further contain any other skin-protective ingredients. For example, it may contain any of anti-inflammatory ingredients of peony, scutellaria roots, St. John's wort, camomile, peach leaves, loquat leaves, mugwort, perilla extract, etc.; moisturizers of silk fibroin, silk sericin, collagen, seaweed extract, etc.; anti-oxidative (deodorant) ingredients of green tea, bamboo extract, etc.; pH controllers of natural fruits acids (malic acid, succinic acid, citric acid, tartaric acid, lactic acid, etc.), alkali metal salts and alkaline earth metal salts (phosphates, carbonates, etc.), etc. These ingredients may be also contained in the support layer 51 to be mentioned below.

The support layer 51 is preferably formed of a compound capable of absorbing moisture or dissolving in water at a relative humidity of at least 30%, more preferably a compound capable of absorbing moisture or dissolving in water at a relative humidity of at least 50%. While the diaper 1 is worn and when the support layer 51 absorbs moisture in the presence of the wearer's sweat and excretions, the support layer 51 is fluidized, and, after the thus-fluidized support layer 51 has moved, the skin-protective ingredient-containing layer 50 is exposed outside. As the case may be, when the support layer 51 absorbs moisture, the ingredient of the layer 50 passes through the support layer 51 and appears on the surface of the support layer 51.

Accordingly, while the diaper 1 is worn, the support layer 51 is kept in contact with the skin of a wearer and protects the layer 50, and only when the skin-protective ingredient is needed, the ingredient-containing layer 50 appears on the surface of the support layer 51 to form the oily film. In that manner, the layer 50 is influenced by the ambient humidity, and changes little even when the ambient temperature only is elevated during storage and transportation of the diapers. Only when the skin-protective ingredient of the layer 50 is really needed by a wearer, it appears on the surface of the diaper to be in contact with the skin of the wearer, and is therefore efficient and is wasted little.

In order that the skin-protective ingredient of the layer 50 certainly appears on the surface of the diaper 1 only when it is needed by the wearer who is wearing the diaper 1, and in order that the thus-exposed ingredient can form an oily film on the surface of the wearer's skin, it is desirable that the support layer 51 is formed of a compound capable of absorbing moisture or dissolving in water at 25° C. or higher, more preferably at 30° C. or higher. However, if the support layer 51 is formed of a compound that could not still absorb moisture or could not still dissolve in water or could not be still fluidized even at temperatures higher than ordinary human body temperature, for example even at 40° C. or higher, the underlying skin-protective ingredient could hardly appear on the surface of the support layer 51 when it is needed. Therefore, it is desirable that the support layer 51 is made of a compound capable of absorbing moisture or capable of dissolving in water or capable of being fluidized at 40° C. or lower, more preferably at 37° C. or lower.

The support layer 51 must protect the layer 50 until the skin-protective ingredient of the layer 50 is needed. For its properties, therefore, the compound to form the support layer 51 is preferably semi-solid (including wax, gel and sol) or solid. After heated to be liquid or semi-solid, the compound is applied to the top sheet 10 of the diaper 1. If the melting point of the compound to form the support layer 51 is too high, the substrate (top sheet) and the underlying, skin-protective ingredient-containing layer 50 to be coated with the support layer 51 will be damaged, and the feel of the diaper 1 will be degraded. Therefore, it is desirable that the melting point of the compound to form the support layer 51 is not higher than 100° C., more preferably not higher than 90° C. When the compound must be firstly dissolved in water and the resulting aqueous solution must be applied to the top sheet 10, the top sheet 10 coated with the solution must be dried to form the intended support layer 51 thereon. In this case, therefore, it is desirable that the compound to form the support layer 51 is not degraded to lower its feel when heated in drying it.

The support layer 51 is kept in direct contact with the skin of a wearer. Therefore, it is undesirable to irritate the skin of a wearer. For example, the human skin in healthy condition generally has a pH of from 4.5 to 7.5. Accordingly, it is desirable that the support layer has a pH of from 4.5 to 7.5, more preferably from 5.0 to 7.0. In addition, since the support layer 51 will adhere to the skin of a wearer, it is desirable that the compound to form the support layer 51 is colorless or white, or is nearly colorless or whitish.

Concretely, it is desirable that the compound to form the support layer 51 is at least one compound selected from the group consisting of polyethylene oxide having a molecular weight of from 100 to 500,000, polypropylene glycol having a molecular weight of from 100 to 10,000, and polyvinyl alcohol having a degree of polymerization of from 300 to 4000 and a degree of saponification of from 50 to 99. Among these, preferred is polyethylene oxide having a molecular weight of from 500 to 3,000, which is solid or semi-solid at room temperature and can be semi-solid or liquid at a temperature falling between 25 and 40° C. or higher; and more preferred is polyethylene oxide having a melting point of from 35 to 40° C. and having a molecular weight of from 700 to 1,000.

When polyvinyl alcohol is used to form the support layer 51, it is desirable to add thereto glycols serving as a plasticizer, such as ethylene glycol, trimethylene glycol, tetramethylene glycol, pentamethylene glycol, hexamethylene glycol, propylene glycol, glycerin, 2,3-butanediol, 1,3-butanediol, diethylene glycol, triethylene glycol or the like. This is to lower the melting point of the support layer 51 and to make the support layer 51 more flexible to thereby reduce the physical stimulation of the support layer 51 to the skin.

The layers 50 and 51 may be formed by applying a predetermined amount of the respective compounds for them onto the top sheet 10 (substrate). For example, they may be applied thereto by printing, such as gravure printing or flexographic printing. As the case may be, a coating technique for thermal adhesives (e.g., a hot-melt adhesive or the like) is also employable. Concretely, the compound to form the layer is melted by use of a hot-melt applicator, and then (1) a predetermined amount of the resulting melt is extruded out by use of a gear pump, and is directly coated on the substrate via a dies kept in contact with the substrate by use of a slot coater; or (2) the melt is extruded out through a dies, and then sprayed over the substrate under air pressure; or (3) the melt is fiberwise extruded out through a dies, and directly bonded to the substrate. Still employable herein is a dyeing technique. Concretely, the substrate is directly dipped in a coating liquid of the compound to form the layer, and the excess coating liquid is squeezed out of the substrate.

Figure 3:
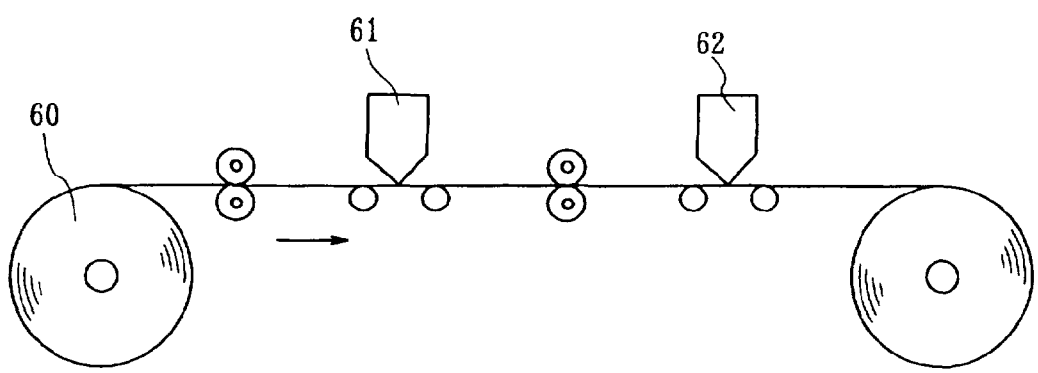
FIG. 3 is a view graphically showing a flowchart for forming a layer containing a skin-protective ingredient and a support layer.
Figure 4A:
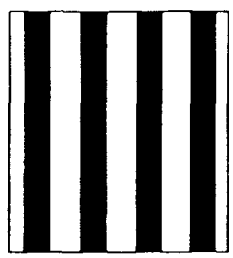
FIGS. 4A, 4B and 4C are plan views of different patterns of the ingredient-containing layer and the support layer.
Figure 4B:
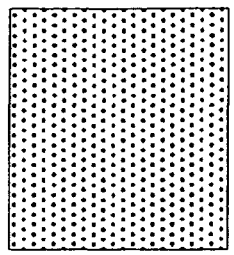
Figure 4C:
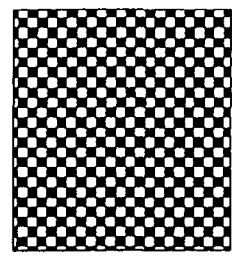

In order to ensure the maximum coating result with a minimum coating amount of the compound to form the intended layer, it is desirable that the coating compound is applied to the uppermost fibrous region of the substrate. To that effect, the printing technique (gravure printing or flexographic printing), as well as the coating technique for thermal adhesives are preferred herein among the techniques set forth above. For example, as shown in FIG. 3, a substrate is fed from a roller 60 and then the substrate is coated with a coating composition fed from a coater 61 to form the layer 50 thereon. With that, the substrate coated with the layer 50 is further coated with another coating composition fed from a coater 62 to form the support layer 51 on the layer 50. The substrate thus coated with the layers 50 and 51 is used for the top sheet of the absorbent article according to the invention. Regarding the coating pattern of the respective layers 50 and 51 thereon, the substrate may be uniformly coated with the layers on its entire surface as shown in FIG. 2. As the case may be, the layers may have a stripe pattern as shown in FIG. 4A, or a dot pattern as shown in FIG. 4B, or a lattice pattern as shown in FIG. 4C.

Figure 5A:
FIGS. 5A, 5B and 5C are cross-sectional views of different embodiments of the constitution of the ingredient-containing layer and the support layer.
Figure 5B:
Figure 5C:

Regarding the structure of the layers 50 and 51, the two layers may be simply laid one upon another as shown in FIG. 2. As the case may be, the layer 50 may be embedded in the support layer 51 as shown in FIG. 5A. In this case, the support layer 51 is firstly formed, this is then coated with the layer 50, and thereafter the layer 50 is further coated with the support layer 51. Thus constructed, the layer 50 is prevented from penetrating into the substrate such as the top sheet. Furthermore, the layer 50 to be located in the middle of the support layer 51 may be discontinuously embedded therein, as shown in FIG. 5B. In this case, the layer 50 may have any one of the patterns of FIG. 4A to FIG. 4C. As the case may be, the layer 50 may be previously exposed partially out of the surface of the support layer 51 as shown in FIG. 5C.

A larger amount of the layer 50, if coated so, will be more effective for protecting the skin of a wearer. In particular, when a water-repellent skin-protective agent is used for the layer 50, the amount to be coated preferably falls between 0.1 and 50 g/m$^2$, more preferably between 1 and 30 g/m$^2$, in order to avoid detracting from the liquid permeability of the top sheet. Also preferably, the amount of the support layer 51 to be coated falls between 0.1 and 50 g/m$^2$, more preferably between 1 and 30 g/m$^2$, in order that the ingredient contained in the layer 50 can appear out of the support layer 51 at the predetermined humidity and temperature.

The top sheet 10 to be coated with the layers 50 and 51 may be made of a non-woven fabric having a unit weight (Metsuke) of from 10 to 60 g/m$^2$, for which, for example, usable are polyolefin or polyester synthetic fibers, semi-synthetic fibers of rayon or the like, or natural fibers of pulp, cotton or the like. The fineness of these fibers may fall between 1.1 and 5.5 dtex. For the top sheet 10, especially preferred is a thermally-bonded non-woven fabric having high strength and good workability. Other non-woven fabrics of hydrophilicated hydrophobic fibers or hydrophilic fibers such as point bonding, air-through, spun bonding or spun lace non-woven fabrics are also usable for the top sheet 10. Further usable for it are perforation webs, which may be prepared by forming a sheet of polyethylene (having a density of from 0.86 to 1.1 g/m$^3$) and/or polypropylene (having a density of from 0.89 to 1.2 g/m$^3$) through extrusion either singly or as combined, followed by perforating the sheet with hot air jets or with hot needles to make the sheet have liquid-pervious through-holes, or by depositing a fiber web on a film followed by perforating the resulting sheet with hot air jets or with hot needles to make the sheet have liquid-pervious through-holes (perforations). Any webs are usable for the top sheet 10, provided that their liquid permeability and absorbability comes up to the standard of JIS L-1092 (testing methods for water resistance of textiles, resistance to water of from 0 to 300 mmH$_2$O in a test method A (low-pressure method) for the degree of resistance to water), and provided that their air permeability comes up to the standard of JIS L-1906 (testing methods for non-woven fabrics made of filament yarn, air transmission rate of from 5 to 700 cm$^3$/cm$^2$/sec in an air permeation test for fragile).

The back sheet 11 is pervious to air but not to liquid, and is formed of, for example, a polyolefin resin sheet. Non-woven fabric may be used for the back sheet 11, with a water-resistant film being sandwiched between the back sheet and the absorbent core. When it is put on any other absorbent articles, the back sheet 11 may be made of a liquid-pervious sheet. In order to ensure the layer formation thereon, the back sheet 11 may have a multi-layer structure (laminate sheet) of which the uppermost layer to be coated shall have the highest density.

The absorbent core 12 may be formed of an absorbent material, for example, powdery pulp or its mixture with high-absorbent polymer. For this, the powdery pulp or its mixture with the high-absorbent polymer may be wrapped with an absorbent sheet of tissue or the like. For example, the fastener portion 17 may be an adhesive tape of rubber adhesive or acrylic resin, etc.; and the fastener sheet 18 may be a resin film.

In the illustrated embodiment, the layers 50 and 51 are present in the entire region of the absorbent core 12, but may be not present in the entire region thereof. For example, the layers 50 and 51 may be provided only in the front area 2A which is fitted to the abdominal region of a wearer and/or in the back area 2C which is fitted to the buttocks and/or the back of a wearer, in order to protect the abdominal region and the buttocks of a wearer from being irritated and in order not to lower the liquid permeability of the top sheet 10. Not limited to these, the layers 50 and 51 may be provided in any other region of the absorbent article 1 that shall be in direct contact with the skin of a wearer.

Figure 6:
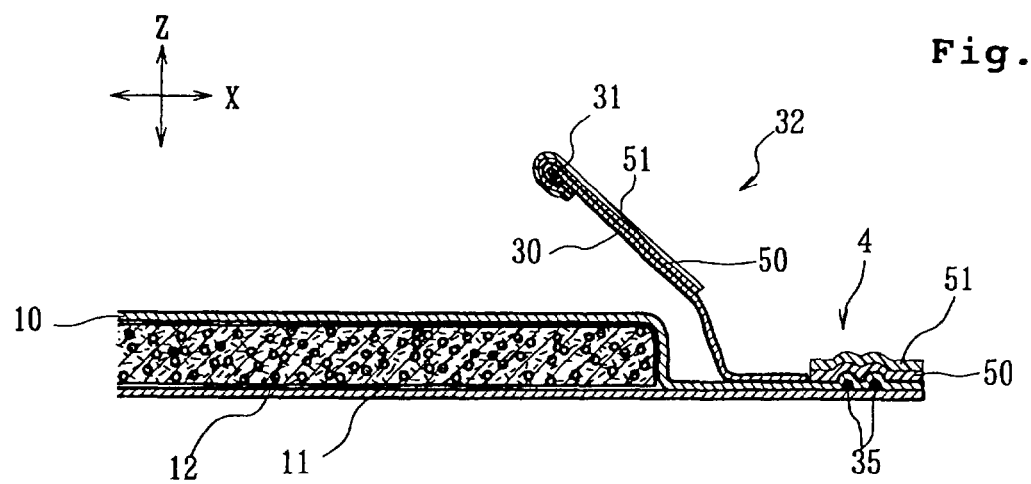
FIG. 6 is a partial cross-sectional view of another embodiment of the absorbent article according to the invention.

FIG. 6 is a partial cross-sectional view of another embodiment of the absorbent article according to the invention. In the leak-preventive cuff 32, the region that shall be in direct contact with the skin of a wearer i.e., the free end side provided with the elastic member 31 is coated with the layers 50 and 51. Furthermore, the respective side edge portions 4 provided with the elastic member 35 to form the leg cuff that shall be in direct contact with the thighs of a wearer, is coated with the layers 50 and 51. In that manner, it is possible to protect the skin around the crotch and the thighs of a wearer from being irritated.

While a wearer is wearing an absorbent article, the skin being in contact with the elastic member of the absorbent article is subjected to much physical stimulation as being always rubbed against the elastic member. Therefore, it is desirable that the skin of the wearer in that region is specifically protected as in the manner illustrated herein. As the case may be, the waist part of the absorbent article provided with the elastic member 16 may be coated with the layers 50 and 51.

Some embodiments of the open diaper have been disclosed herein for the absorbent article of the invention. Not limited to these, the invention is applicable to any other types of the absorbent articles such as panty-type diapers, incontinence pads, sanitary napkins, pantiliners, etc.

In the absorbent article of the invention, the support layer is sensitive to moisture and protects the skin-protective ingredient-containing layer before the moisture in the absorbent articles increases to the intended level. In this, therefore, the skin-protective ingredient can be released and adheres to the skin of a wearer only when the moisture in the absorbent article has increased to the intended level, or that is, only when the ingredient becomes necessary for the wearer, and, in addition, the thus-released ingredient adheres only to the skin of the wearer to be protected therewith but not to any other region, and is therefore wasted little.

When the support layer is formed of a water-soluble substance, it will hardly retard the liquid permeability of the top sheet.

While the invention has been described in detail and with reference to specific embodiments thereof, it will be apparent to one skilled in the art that various changes and modifications can be made therein without departing from the spirit and scope thereof.

Here, 'comprises/comprising' when used in this specification is taken to specify the presence of stated features, integers, steps or components but does not preclude the presence or addition of one or more other features, integers, steps, components or groups thereof.

What is claimed is:

1. An absorbent article comprising:
    a main body including a liquid-pervious top sheet, a back sheet and an absorbent core sandwiched between said top sheet and said back sheet;
    a skin-protective ingredient containing layer on one surface of said top sheet such that a skin-protective ingredient is released from said one surface of said top sheet and transferred to skin of a wearer to form an oily film on the skin of the wearer, said skin-protective ingredient containing layer being in a liquefied state at 35° C. or higher; and
    a support layer substantially entirely and directly coating said skin-protective ingredient containing layer for retaining said skin-protective ingredient on said one surface of said top sheet and isolating said skin-protective ingredient containing layer from the skin of the wearer, said support layer being formed of polyethylene oxide,
    wherein the support layer absorbs moisture at a relative humidity of 30%, and is fluidized, and, after the thus-fluidized support layer has moved, the skin-protective ingredient containing layer is exposed to the wearer's skin, and
    wherein said skin-protective ingredient containing layer is formed of at least one compound selected from the group consisting of liquid polyisoprene, squalane, pristine, ozocerite, ceresine, microcrystalline wax, polyethylene powder, liquid paraffin, petroleum jelly and paraffin.

2. The absorbent article as set forth in claim 1, further including:
    at least one of a leak-preventive cuff for preventing side leakage and leg cuff for preventing leakage through an area around a wearer's thighs, and the at least one of a leakage-preventive cuff and leg cuff are located between said top sheet and said skin-protective ingredient containing layer and said support layer.

3. The absorbent article as set forth in claim 1, wherein said skin-protective ingredient containing layer and said support layer are provided in regions of the absorbent article that are fitted to the thighs of the wearer.

4. The absorbent article as set forth in claim 1, wherein said skin-protective ingredient containing layer and said support layer are provided in regions of the absorbent article that are fitted to one or more of the back, the buttocks or the abdominal region of the wearer.

5. The absorbent article according to claim 1, wherein the support layer consists essentially of a material that absorbs moisture at a relative humidity of 30%.

6. The absorbent article according to claim 5, wherein the support layer consists essentially of polyethylene oxide.

7. The absorbent article according to claim 1, wherein the polyethylene oxide has a molecular weight of from 700 to 1,000 and having a melting point from 35° C. to 40° C.

8. An absorbent article comprising:
    a main body including a liquid-pervious top sheet, a back sheet and an absorbent core sandwiched between said top sheet and said back sheet;
    a skin-protective ingredient containing layer on one surface of said top sheet such that a skin-protective ingredient is released from said one surface of said top sheet and transferred to skin of a wearer to form an oily film on the skin of the wearer, said skin-protective ingredient containing layer being in a liquefied state at 35° C. or higher; and
    a support layer substantially entirely and directly coating said skin-protective ingredient containing layer for retaining said skin-protective ingredient on said one surface of said top sheet and isolating said skin-protective ingredient containing layer from the skin of the wearer, said support layer being formed of polyethylene oxide,
    wherein the support layer absorbs moisture at a relative humidity of 50%, and is fluidized, and, after the thus-fluidized support layer has moved, the skin-protective ingredient containing layer is exposed to the wearer's skin, and
    wherein said skin-protective ingredient containing layer is formed of at least one compound selected from the group consisting of liquid polyisoprene, squalane, pristine, ozocerite, ceresine, microcrystalline wax, polyethylene powder, liquid paraffin, petroleum jelly and paraffin.

* * * * *